United States Patent [19]

Espy

[11] Patent Number: 4,458,042
[45] Date of Patent: Jul. 3, 1984

[54] ABSORBENT MATERIAL
[75] Inventor: Herbert H. Espy, Wilmington, Del.
[73] Assignee: Hercules Incorporated, Wilmington, Del.
[21] Appl. No.: 477,120
[22] Filed: Mar. 21, 1983
[51] Int. Cl.³ .......................... C08L 97/02; C08L 9/00; D21F 11/00; D21H 5/18
[52] U.S. Cl. ........................................ 524/14; 524/13; 524/502; 524/543; 162/142; 162/146; 162/169; 162/182
[58] Field of Search ................... 524/13, 14, 502, 543; 523/220; 162/142, 146, 169, 182

[56] References Cited
U.S. PATENT DOCUMENTS

| | | | |
|---|---|---|---|
| 4,049,493 | 9/1977 | Lare | 162/182 |
| 4,082,886 | 4/1978 | Butterworth et al. | 428/284 |
| 4,156,628 | 5/1979 | Rave | 162/182 |
| 4,257,842 | 3/1981 | Ciaccia et al. | 162/146 |
| 4,286,030 | 8/1981 | Moore | 429/253 |
| 4,289,580 | 9/1981 | Elston et al. | 162/146 |
| 4,296,168 | 10/1981 | Ambrose | 428/288 |
| 4,319,956 | 3/1982 | Snyder et al. | 162/146 |

Primary Examiner—John Kight, III
Assistant Examiner—Nathan M. Nutter
Attorney, Agent, or Firm—Jeffrey F. Craft

[57] ABSTRACT

Disclosed is absorbent material composed of a consolidated blend of spurted polyolefin pulp, treated with an anionic or nonionic wetting agent substance having a molecular weight less than about 8000, and wood fluff pulp. The absorbent material exhibits a desirable combination of strength, rate of absorbency and total absorbency.

8 Claims, No Drawings

ABSORBENT MATERIAL

BACKGROUND OF THE INVENTION

1. Field of the Invention

This invention relates to an improved absorbent material composed of a consolidated blend of spurted polyolefin and wood fluff pulps. In particular, the invention relates to an absorbent material composed of spurted polyolefin pulp, treated with an anionic or nonionic wetting agent substance having a molecular weight less than about 8000, blended with wood fluff pulp and consolidated by heating at a temperature and for a time sufficient to fuse the treated spurted polyolefin pulp.

2. Description of the Prior Art

Wood fluff pulp has gained widespread acceptance as an absorbent material. Because wood fluff pulp exhibits excellent bulk, softness, and high absorbency, it is used in a wide variety of products such as disposable diapers, feminine care products and the like. Unfortunately, wood fluff pulp does not have good strength, and products made of wood fluff pulp have a marked tendency to disintegrate under low stress.

SUMMARY OF THE INVENTION

Now it has been found that where a spurted polyolefin pulp, treated with an anionic or nonionic wetting agent substance having a molecular weight less than about 8000, is blended with wood fluff pulp and the blend is consolidated by heating at a temperature and for a time sufficient to fuse the spurted polyolefin pulp, the resulting absorbent material exhibits good strength without any sacrifice in absorbency. In fact, it has been found that the consolidated blend exhibits greater absorbency than its unconsolidated counterpart.

The absorbent material is comprised of a consolidated blend consisting essentially of wood fluff pulp and treated spurted polyolefin pulp at about 3 to about 30%, based on the total weight of the blend, which treated spurted polyolefin pulp has been treated with from about 0.05 to about 3%, preferably from about 0.1 to about 1%, based on the weight of the spurted polyolefin pulp of a wetting agent substance selected from the group consisting of nonionic and anionic wetting agents, each of which has a molecular weight less than about 8000.

DETAILED DESCRIPTION OF PREFERRED EMBODIMENTS

Improved absorbent material is formed by blending wood fluff pulp and spurted polyolefin pulp which has been treated with a wetting agent substance, and then heating the blend at a temperature and for a time sufficient to consolidate the treated spurted polyolefin pulp.

The major component, by weight, of the improved absorbent material is wood fluff pulp. The grades of wood fluff pulp and the methods of its preparation are known to those skilled in the art.

Wood pulp can be obtained from well known chemical processes such as the kraft and the sulfite processes. For these processes, the best starting material is prepared from long fiber coniferous wood species, such as pine, douglas fir, blue fir, spruce, and hemlock. Wood pulp also can be obtained from mechanical processes, such as ground wood, refiner mechanical, thermomechanical, chemimechanical, and chemithermomechanical pulp processes. Details of the production and use of wood pulp are well known to one skilled in the art.

The other critical component of the improved absorbent material is treated spurted polyolefin pulp. Spurted polyolefin pulps also are well known in the art. See, e.g. "Pulp, Synthetic", Kirk-Othmer, *Encyclopedia of Chemical Technology*, 3rd ed. (New York: 1982) vol. 19, pp. 420–435.

Spurted polyolefin pulps are very fine highly branched, discontinuous fibrils made from thermoplastic polymers. Their visual appearance and dimensions closely resemble those of wood pulps. Spurted polyolefin pulps have a large surface area (ca. 3–50 $m^2/g$), low densities (ca 0.2 g/cc as measured by mercury porosimetry for spurted polypropylene and ca 0.4 g/cc for spurted polyethylene), an average length of about 1 mm and an average diameter of about 5–40 microns.

Representative of the polymers from which the spurted polyolefin pulps are made are polyethylene, polypropylene, copolymers of ethylene and propylene, copolymers of propylene and other 1-olefins such as 1-butene, 4-methyl-pentene-1 and 1-hexene. Also useful are grafted spurted polyolefin pulps in which maleic anhydride or styrene groups are grafted into any of the above polymers. In some embodiments, the spurted polyolefin pulps are composed solely of one of these polymers. In other embodiments, they are composed of mixtures of two or more of these polymers. The preferred spurted polyolefin pulps are those prepared from polyethylene.

The amount of spurted polyolefin pulp to be used in the blend is from about 3 to about 30% based on the total weight of the blend. The optimal amount for a particular blend will depend on the spurted polyolefin pulp chosen and the properties desired in the final absorbent material. Generally, it has been found that as the percentage of spurted polyolefin pulp increases, the strength of the absorbent material also increases.

The spurted polyolefin pulp is treated with a wetting agent substance. A wetting agent substance is a surface-active agent which reduces the surface tension of water, as water comes into contact with the treated material, thus causing the water to more readily penetrate.

The wetting agent substance in some embodiments comprises just one wetting agent substance selected from the group of an anionic and nonionic wetting agent substances each having molecular weights less than about 8000. In other embodiments it comprises two or more such wetting agent substances. Representative wetting agent substances include polyoxyethylene monostearate ester, bis(hydroxyethyl) tallow amine, sodium dioctyl sulfosuccinate, polyoxyethylene dioleate ester, sodium lauryl sulfate, ethoxylated sorbitan laurate, sodium alkyl sulfonates and the like. Ethoxylated sorbitan laurate and sodium alkyl sulfonates are preferred. Not all wetting agent substances work. For example, it has been found that polyvinyl alcohol, a high molecular weight wetting agent substance, widely used in the industry, can adversely effect the absorbency of the final product.

The wetting agent substance treatment of spurted polyolefin pulp is done in a variety of ways which are known in the art. A preferred method is to spurt the polyolefin pulp directly into an aqueous solution containing the wetting agent substance, under which conditions the wetting agent substance is absorbed onto the surface of the fiber. Other methods include spraying a solution of the wetting agent substance onto the pulp, or adding the wetting agent substance to the pulp slurry during the blending process. Other methods will be apparent to those skilled in the art.

The treatment is such that from about 0.05 to about 3%, preferably from about 0.1 to about 1%, based on the weight of the spurted polyolefin pulp, of the wetting agent substance is retained in the spurted polyolefin pulp. Where less wetting agent substance is retained, the absorbency properties are inadequate; and where more wetting agent substance is retained, it can interfere substantially with the strength of the final product. The amount of wetting agent substance which is retained on the spurted polyolefin pulp can be controlled by varying the concentration of the wetting agent substance solution used in the treatment or by varying the surface area of the synthetic pulp or by varying both.

In one embodiment the wood pulp and the treated spurted polyolefin pulp are blended by any of the known blending methods. Such methods include the preparation of a pulp sheet by conventional paper-making procedures or by conventional dry blending methods.

After blending, the spurted polyolefin and wood pulps are fluffed and formed into a fluff pad by conventional methods such as hammermilling or air forming.

In other embodiments the spurted polyolefin and wood pulps may be fluffed prior to blending. The order of fluffing and blending is not critical.

Finally, the fluff pad is consolidated by heating at a temperature and for a time sufficient to fuse the spurted polyolefin pulp. It has been found that consolidation not only improves the strength but improves the absorbency of the fluff pad. Fusion will occur by raising the temperature of the fluff pad above the spurted polyolefin pulp's melting point. For example, the melting point of some types of spurted polyethylene pulp is 115° C., while the melting point of spurted polypropylene pulp is 160°–165° C. Methods used to fuse the spurted polyolefin pulp are known in the art. Representative methods include the use of calenders, infrared heaters and pull-through driers and the like. Exact conditions, which will be readily ascertained by one skilled in the art, must be determined for the specific blend being used. The time, which will be readily ascertained by one skilled in the art, generally ranges from 1 second to about 10 minutes.

The best mode now contemplated of carrying out this invention is exemplified by the following working examples of preferred specific embodiments of this invention. This invention is not limited to these specific examples.

In these examples the rate of absorbency and the total absorbency are measured by the method taught in INDA Symposium Papers covering the Technical Symposium held on Mar. 5–6, 1974 on Nonwoven Product Technology, pages 129–149. All percentages are based on weight unless otherwise clearly indicated. Tensile strength is determined on a two inch wide strip of the blend.

EXAMPLES 1–5

Preparation of Treated Spurted Polyolefin Pulp

These examples illustrate preferred embodiments of absorbent material based on ethoxylated sorbitan monolaurate-treated spurted polyethylene pulp and bleached softwood kraft pulp, in which the blend is water-laid and then hammer milled to form a fluff pad which is consolidated.

Sufficient high density polyethylene is dissolved in hexane to make a solution containing, by weight, 12% polyethylene. The solution is heated to a temperature of 140° C. and a pressure of 1500 psi is established and maintained. The resulting solution is spurted into a flash tank containing 0.7% ethoxylated sorbitan monolaurate (having a molecular weight less than 8000), based on the weight of the synthetic pulp. The resulting spurted polyethylene pulp is dewatered to give a wet lap of approximately 42% solids. Analysis by isopropanol extraction shows a wetting agent substance concentration of 0.65% on a dry basis.

Forming Blend

Treated spurted polyethylene pulp, prepared as described above, is blended with bleached softwood kraft pulp in varying proportions by dispersing both in water at about 2% consistency, and then formed into sheets, dewatered and dried with conventional paper making equipment. The amounts of spurted polyethylene and wood pulp in the blends and the density of the resulting pads are shown in Table 1.

The pulp sheets are hammermilled into fluff pads using a conventional hammermill such as that used in the preparation of disposable diapers.

The fluff pads are placed in an oven at 150° C. for 10 minutes to fuse the treated spurted polyolefin pulp.

The rate of absorbency and total absorbency of a 1% saline solution in each example is determined and typical results are shown in Table 1.

TABLE 1

| Example | % Treated Polyethylene Pulp | Pad Density (g/cm$^3$) | Demand Wettability | | |
|---|---|---|---|---|---|
| | | | Capacity (ml/g) | Time to Capacity (min.) | % Capacity in 60 sec. |
| 1 | 0 | 0.022 | 12.1 | 0.4 | 100 |
| 2 | 5 | 0.020 | 13.2 | 0.75 | 100 |
| 3 | 10 | 0.023 | 13.6 | 0.90 | 100 |
| 4 | 20 | 0.022 | 13.7 | 1.0 | 100 |
| 5 | 50 | 0.025 | * | * | * |

*Measurement could not be made for orifice plugs.

EXAMPLE 6

This example illustrates a preferred embodiment of absorbent material based on a blend of ethoxylated sorbitan monolaurate-treated spurted polyethylene pulp and bleached softwood kraft fluff pulp in which the blend is air laid to form a fluff pad and then consolidated. Treated spurted polyolefin pulp wet lap is formed as described above. The wet lap is then dried at ambient temperature, broken into pieces and preblended in a bag with bleached soft wood kraft fluff pulp. Final blending is achieved by passing the preblend through a Fitz mill.

Using conventional equipment, the blend is then air laid. The blend contains twenty percent spurted polyolefin pulp. The density of the air laid pad is shown in Table 2. The pad is then placed in an oven at 300° F. for 10 minutes. Typical absorbency properties are reported in Table 2. For comparison, typical results are shown for a control in which no spurted polyolefin pulp is employed in the absorbent pad.

TABLE 2

| Example | Pad Density (g/cm³) | Demand Wettability | | |
|---|---|---|---|---|
| | | Capacity (ml/g.) | Time to Capacity (min.) | % Capacity in 60 sec. |
| Control | 0.014 | 13.4 | 0.5 | 100 |
| 6 | 0.013 | 14.1 | 0.8 | 100 |

EXAMPLE 7

This example illustrates a preferred embodiment in which the blend of Example 6 is consolidated in a platen press.

The blend of Example 6 is consolidated in a platen press at 150° C. under low pressure for two minutes. Typical strength and absorbency properties are shown in Table 3. For comparison typical results are shown for a control in which no spurted polyolefin pulp is employed in the absorbent pad.

TABLE 2

| Example | Pad Density (g/cm³) | Demand Wettability | | | Tensile Strength (psi) |
|---|---|---|---|---|---|
| | | Capacity (ml/g.) | Time to Capacity (min.) | % Capacity in 60 sec. | |
| Control | 0.027 | 11.9 | 0.6 | 100 | 0.035 |
| 7 | 0.043 | 12.0 | 0.7 | 100 | 2.1 |

By following the above procedures, one skilled in the art will be able to form, without undue experimentation, absorbent material containing any of the disclosed spurted polyolefin fluff pulps treated with any of the disclosed wetting agent substances.

Other features, advantages, and specific embodiments of this invention will become readily apparent to those exercising ordinary skill in this art after reading the aforegoing disclosure. In this connection, the specific embodiments of this invention have been described in considerable detail. Variations and modifications of these embodiments can be effected without departing from the spirit and scope of the invention as disclosed and claimed.

What I claim and desire to protect by Letters Patent is:

1. An absorbent material comprising a consolidated blend consisting essentially of wood fluff pulp and from about 3 to about 30%, based on the total weight of the consolidated blend, spurted polyolefin pulp, where the spurted polyolefin pulp is treated from about 0.05 to about 3%, based on the weight of the spurted polyolefin pulp, of a nonionic or an ionic wetting agent substance having a molecular weight less than about 8000.

2. The consolidated blend of claim 1 wherein the spurted polyolefin pulp is spurted polyethylene pulp.

3. The consolidated blend of claim 1 wherein the spurted polyolefin pulp is spurted polypropylene pulp.

4. The consolidated pulp of claim 1 wherein the wetting agent is chosen from the group consisting of polyoxyethylene monostearate ester, bis(hydroxyethyl)tallow amine, sodium dioctyl sulfosuccinate, polyoxyethylene dioleate ester, ethoxylated sorbitan laurate, sodium alkyl sulfonate, and sodium lauryl sulfate.

5. The absorbent material of claim 2 wherein the wetting agent is ethoxylated sorbitan laurate.

6. The absorbent material of claim 2 wherein the wetting agent is sodium alkyl sulfonate.

7. The absorbent material of claim 3 wherein the wetting agent is ethoxylated sorbitan laurate.

8. The absorbent material of claim 3 wherein the wetting agent is sodium alkyl sulfonate.

* * * * *